United States Patent [19]

Tesk et al.

[11] 3,948,653

[45] Apr. 6, 1976

[54] NOVEL NONPRECIOUS ALLOY SUITABLE FOR FUSION TO PORCELAIN

[75] Inventors: John Aloysius Tesk, Woodridge; Ronald Peter Dudek, River Grove; Peter Kosmos, Alsip, all of Ill.

[73] Assignee: Howmedica, New York, N.Y.

[22] Filed: June 2, 1975

[21] Appl. No.: 582,761

[52] U.S. Cl. ................................. 75/171; 148/32
[51] Int. Cl.² ................................. C22C 19/05
[58] Field of Search ........ 75/171, 170; 148/32, 32.5

[56] References Cited
UNITED STATES PATENTS
3,841,868   10/1974   Dudek et al. ...................... 75/171

*Primary Examiner*—R. Dean
*Attorney, Agent, or Firm*—Connolly and Hutz

[57] ABSTRACT

A nonprecious alloy for fixed dental restorations such as for porcelain fused to metal, plastic veneered crown and bridge, nonveneered crown and bridge, inlays, etc. includes the following ranges of constituents in percentages by weight:

| Constituent | Proportional Range |
|---|---|
| Nickel | Balance |
| Chromium | 12–15% |
| Aluminum | 0–1% |
| Silicon | 0–1% |
| Tin | 0–1.25% |
| Manganese | 0.01–0.75% |
| Gallium | 4.5–8% |
| Molybdenum | 5–8% |
| Iron | 3–10% | with the proviso that the combined percentage of tin, gallium and silicon must be at least 5.75%.

8 Claims, No Drawings

NOVEL NONPRECIOUS ALLOY SUITABLE FOR FUSION TO PORCELAIN

BACKGROUND OF THE INVENTION

A metal alloy for making a dental restoration must be strong, tough, resistant to tarnish, oxidation and corrosion, compatible with the human oral environment (biocompatible), have good castability and, if used with porcelain, have a suitable coefficient of thermal expansion to be fusible to porcelain.

Effective dental alloys can be divided into two groups depending upon whether or not they contain precious metals. Those containing such metals are relatively expensive because of their high precious metal content. Nonprecious alloys are generally inferior in handling characteristics to precious alloys, usually having an undesirably high (230–320 BHN) hardness, and are generally relatively hard to cast, grind, or otherwise finish. In addition, when using such alloys it is frequently hard to produce castings giving a good fit to a metal die. An object of this invention is to provide a highly effective and relatively simple and economical nonprecious alloy suitable for dental use including fusibility to porcelain.

SUMMARY OF THE INVENTION

In accordance with this invention one highly effective and reasonably economical nonprecious alloy for porcelain fused to metal dental prosthesis incorporates the following ranges of constituents in percentages by weight:

| Constituent | Proportional Range |
| --- | --- |
| Nickel | Balance |
| Chromium | 12–15% |
| Aluminum | 0–1% |
| Silicon | 0–1% |
| Tin | 0–1.25% |
| Manganese | 0.01–0.75% |
| Gallium | 4.5–8% |
| Molybdenum | 5–8% |
| Iron | 3–10% | with the proviso that the combined percentage of tin, gallium and silicon must be at least 5.75%.

DETAILED DESCRIPTION OF THE INVENTION

Particular examples of the alloys of this invention especially for fusion to porcelain are listed below in Examples I–V giving preferred compositions in percentages by weight. These alloys have been found particularly useful for dental service and are particularly effective for fusion and tight adherance to porcelain.

Especially preferred is the following alloy:

| Constituent | Composition |
| --- | --- |
| Nickel | 66.65% |
| Chromium | 13% |
| Molybdenum | 7% |
| Silicon | 0.75% |
| Manganese | 0.10% |
| Iron | 5% |
| Gallium | 7.5% |

A suitable method for porcelain application to a cast metal framework prepared from an alloy of the present invention is as follows:

1. The alloy casting has its surface prepared for preconditioning by removing casting oxides and residual investment by grinding.
2. The cast alloy prosthesis is preconditioned by placing it in a furnace at 1400°F. and firing it from 1400° to 2000°F. in air at the rate of 80°–100°F. per minute, then removing and allowing it to cool to room temperature.
3. A thin wash of opaque porcelain is applied to the areas which are to receive porcelain and the prosthesis is fired from 1700° to 2000°F. in air, at 80°–100°F. per minute, soaked for 1 minute at 2000°F. and then removed and allowed to cool to room temperature.
4. A second layer of opaque porcelain is applied and the prosthesis is fired from 1400° to 1700°F. in air at 80°–100°F. per minute and soaked for 1 minute at 1700°F. Following the firing cycle, the prosthesis is allowed to cool to room temperature.

The porcelain is for example, Microbond Hi-Life Body Porcelain. "Hi-Life" and "Microbond" are trademarks of Howmedica Inc., Dental Division, Chicago, Ill. for a porcelain having approximately the following formulation in percentages by weight:

| Constituent | Composition |
| --- | --- |
| $SiO_2$ | 68.64% |
| $Al_2O_3$ | 13.76% |
| CaO | 0.36% |
| $K_2O$ | 13.46% |
| $Na_2O$ | 2.29% |
| $Li_2O$ | 1.49% |

Other porcelains intended for fabrication of fused porcelain prosthesis and having a softening point of about 1200°–1400°F. may be substituted.

5. Body porcelain and incisal porcelain are then applied and fired according to the appropriate technique for the particular porcelain employed.

The alloys of the present invention are also well suited for the preparation of plastic veneered crowns and bridges, non-veneered crown and bridge dental restorations, inlays and the like.

In casting the alloys of the present invention, it is prudent to employ the known precautions applicable in casting all non-precious alloys, to take into account their lower densities and lower thermal conductivity compared with precious metals. As is known, these precautions and techniques include use of large casting reservoirs (to compensate for low density in centrifugal casting) and use of sprue or gate reservoirs (to compensate for lower heat conductivity which tends to permit sprues to solidify prematurely).

For an enhanced bond between the porcelain and the alloy up to 1% aluminum may be added. However, where maximum visual castability is required, up to 0.125% aluminum is preferred.

These alloys were designed for use as an understructure onto which porcelain is fused for making a fixed bridge type of dental restoration. General characteristics of these alloys are:

1. Ability to successfully melt and cast using either an oxy/acetylene torch or propane-oxygen torch or natural gas-oxygen torch or an induction type casting machine.
2. Precision dental castings can be achieved when cast into dental investments.
3. A matching range of coefficients of thermal expansion between the alloys and the porcelains.

4. Corrosion resistance to oral cavity fluids, and tissue tolerance.
5. As cast Brinell Hardness values in the range of about 130–180.
6. Mechanical properties sufficient to withstand the forces employed in the mouth during mastication.

Aside from the practical evaluation of these alloys which involved the construction of porcelain fused to metal bridges, the following specific properties were determined in the manner described below:

Coefficient of Thermal Expansion
Equipment — Theta Dilatronic I, automatic recording dilatometer.
Test specimen — 2.000 inches long × 0.250 inch diameter
Test method — Determine the coefficient of thermal expansion between 200° and 1200°F.

Hardness
Equipment — Rockwell Hardness tester
Test specimen — case piece ½ × ¾ × ⅛ inch thick.
Test method — the hardness numbers were determined in three states:
1. As Cast Condition
2. Annealed — quenched after heating for 10 minutes at 1290°F.
3. Heat treated — 1800°F. for 30 minutes followed by a slow air cool.

Conversion to Brinell hardness via conversion chart for this type of alloy.

Tensile Properties
Equipment — Instron Tensile Machine
Test Specimen: cast piece 2⅞ inch long with 12024 threaded ends and a radius of ¼ inch from the threaded portion to the test area. The test area is 1-inch long with a diameter of 0.09 ± .01 inch diameter. NOTE: This is the specimen described by the ADA in Specification No. 14.

Corrosion and Tarnish Resistance
Adequate corrosion resistance was determined through a compilation of results of tests involving implant studies, in-vitro corrosion resistance vs. a negative control, and through clinical evaluations.

Tarnish resistance is evaluated by exposure to a dilute iodine-alcohol solution at 37°C.

The following properties were determined from the aforementioned tests:

The alloy of Example I for instance, gives the following results:

| As Cast Condition | |
| --- | --- |
| Proportional Limit (psi) | 43,000 |
| 0.2 Yield Stress (psi) | 51,000 |
| Ultimate Tensile Strength (psi) | 71,000 |
| Elongation (%) | 8 |
| Hardness, B.H.N. | 159 |
| Thermal Expansion (in/in °F.) | $8.45 \times 10^{-6}$ |
| Heat treated | |
| Proportional Limit (psi) | 30,000 |
| 0.2% Yield Strength (psi) | 37,000 |
| Ultimate Tensile Strength (psi) | 64,000 |
| Elongation (%) | 13.0 |
| Hardness, B.H.N. | 148 |

The following examples are merely illustrative and in no way limit the scope of the claims.

| EXAMPLE I | |
| --- | --- |
| Constituent | Composition |
| Nickel | 66.65% |
| Chromium | 13% |
| Molybdenum | 7% |
| Silicon | .75% |
| Manganese | .1% |
| Iron | 5% |
| Gallium | 7.5% |
| Thermal Expansion (in/in °F.) | $8.45 \times 10^{-6}$ |
| Brinell Hardness   As Cast | Heat treated |
| 159 | 148 |

| EXAMPLE II | |
| --- | --- |
| Constituent | Composition |
| Nickel | 65.4% |
| Chromium | 13.5% |
| Molybdenum | 7% |
| Tin | 1% |
| Silicon | .5% |
| Manganese | .1% |
| Iron | 5% |
| Gallium | 7.5% |
| Thermal Expansion (in/in °F.) | $8.55 \times 10^{-6}$ |
| Brinell Hardness   As Cast | Heat treated |
| 176 | 162 |

| EXAMPLE III | |
| --- | --- |
| Constituent | Composition |
| Nickel | 65.9% |
| Chromium | 13.5% |
| Molybdenum | 7% |
| Silicon | 1% |
| Manganese | 0.1% |
| Iron | 5% |
| Gallium | 7.5% |
| Thermal Expansion (in/in °F.) | $8.52 \times 10^{-6}$ |
| Brinell Hardness   As Cast | Heat treated |
| 176 | 165 |

| EXAMPLE IV | |
| --- | --- |
| Constituent | Composition |
| Nickel | 67.4% |
| Chromium | 13.5% |
| Molybdenum | 6% |
| Aluminum | 0.5% |
| Gallium | 7.5% |
| Manganese | 0.1% |
| Iron | 5% |
| Thermal Expansion (in/in °F.) | $8.43 \times 10^{-6}$ |
| Brinell Hardness   As Cast | Heat treated |
| 153 | 121 |

| EXAMPLE V | |
| --- | --- |
| Constituent | Composition |
| Nickel | 68.65% |
| Chromium | 13.5% |
| Molybdenum | 7% |
| Gallium | 5% |
| Silicon | 0.75% |
| Manganese | 0.1% |
| Iron | 5% |
| Thermal Expansion (in/in°F.) | $8.46 \times 10^{-6}$ |
| Brinell Hardness   As Cast | Heat treated |
| 132 | 144 |

What is claimed is:

1. A nonprecious alloy consisting essentially of the following constituents in the indicated percentages by weight:

| Constituent | Proportional Range |
| --- | --- |
| Chromium | 12–15% |
| Aluminum | 0–1% |
| Silicon | 0–1% |
| Tin | 0.00–1.25% |
| Manganese | 0.01–0.75% |
| Gallium | 4.5–8% |
| Molybdenum | 5–8% |
| Iron | 3–10% |
| Nickel | Balance | with the proviso that the combined percentage of tin, gallium and silicon must be at least 5.75%.

2. The alloy of claim 1 containing about .1% manganese.

3. The alloy of claim 1 containing about 7.5% gallium.

4. The alloy of claim 1 containing about 7% molybdenum.

5. The alloy of claim 1 containing about 5% iron.

6. The alloy of claim 1 containing about 13.5% chromium.

7. The alloy of claim 1 consisting essentially of the following constituents in the indicated ranges of percentages by weight.

| Constituent | Proportional Range |
| --- | --- |
| Nickel | 66.65% |
| Chromium | 13% |
| Molybdenum | 7% |
| Silicon | 0.75% |
| Manganese | 0.1% |

| Constituent | Proportional Range |
| --- | --- |
| Iron | 5% |
| Gallium | 7.5%. |

8. The alloy of claim 1 consisting of the following constituents in approximately the indicated percentages by weight:

| Constituent | Composition |
| --- | --- |
| Nickel | 65.4% |
| Chromium | 13.5% |
| Molybdenum | 7% |
| Tin | 1% |
| Manganese | 0.1% |
| Iron | 5% |
| Gallium | 7.5% |
| Silicon | 0.5%. |

* * * * *